United States Patent
McConnell et al.

(10) Patent No.: US 10,444,248 B2
(45) Date of Patent: Oct. 15, 2019

(54) KIDNEY DISEASE BIOMARKER

(71) Applicant: Randox Laboratories Ltd., Northern Ireland (GB)

(72) Inventors: Ivan McConnell, Northern Ireland (GB); Stephen Peter Fitzgerald, Northern Ireland (GB); John Lamont, Northern Ireland (GB); Claran Richardson, Northern Ireland (GB)

(73) Assignee: Randox Laboratories Ltd. (GB)

( * ) Notice: Subject to any disclaimer, the term of this patent is extended or adjusted under 35 U.S.C. 154(b) by 976 days.

(21) Appl. No.: 14/421,382

(22) PCT Filed: Aug. 12, 2013

(86) PCT No.: PCT/GB2013/052148
§ 371 (c)(1),
(2) Date: Feb. 12, 2015

(87) PCT Pub. No.: WO2014/027188
PCT Pub. Date: Feb. 20, 2014

(65) Prior Publication Data
US 2015/0219670 A1      Aug. 6, 2015

(30) Foreign Application Priority Data
Aug. 13, 2012   (GB) .................................. 1214440.8

(51) Int. Cl.
*G01N 33/48*   (2006.01)
*G01N 33/68*   (2006.01)
(Continued)

(52) U.S. Cl.
CPC ....... *G01N 33/6893* (2013.01); *C07K 14/475* (2013.01); *C07K 14/8139* (2013.01);
(Continued)

(58) Field of Classification Search
None
See application file for complete search history.

(56) References Cited

FOREIGN PATENT DOCUMENTS

| EP | 2568291 | * | 3/2013 | ............. G01N 33/68 |
| WO | WO 2010/048346 | * | 4/2010 | ............. G01N 33/48 |

* cited by examiner

*Primary Examiner* — Larry D Riggs, II
(74) *Attorney, Agent, or Firm* — Gavrilovich, Dodd & Lindsey LLP

(57) ABSTRACT

The present invention provides a method of stratifying a patient suffering from CKD into one of stages 1-3 of CKD, comprising determining the level of the biomarkers FABP1, γ-GT, AST, creatinine and cystatin C in a sample obtained from the patient and comparing the level of FABP1 in the sample to a control value and the levels of γ-GT, AST, creatinine and cystatin C in the sample to a range of control values for each biomarker, wherein an increased level of FABP1 compared to the control value and levels of γ-GT, AST, creatinine and cystatin C within the range of control values for each biomarker indicate that the patient suffers from stage 1 CKD or wherein an increased level of FABP1 compared to the control value, levels of γ-GT and AST within the range of control values for each biomarker, and increased levels of creatinine and cystatin C compared to an upper threshold of the control range for these biomarkers indicate that the patient suffers from stage 2 or stage 3 CKD.

17 Claims, 10 Drawing Sheets

(51) Int. Cl.
  *C12N 9/10*      (2006.01)
  *G01N 33/70*     (2006.01)
  *G01N 33/92*     (2006.01)
  *C07K 14/81*     (2006.01)
  *C07K 14/475*    (2006.01)
  *G01N 33/573*    (2006.01)

(52) U.S. Cl.
  CPC ........... *C12N 9/104* (2013.01); *G01N 33/573* (2013.01); *G01N 33/6845* (2013.01); *G01N 33/70* (2013.01); *G01N 33/92* (2013.01); *G01N 2333/47* (2013.01); *G01N 2333/8139* (2013.01); *G01N 2333/9108* (2013.01); *G01N 2333/91188* (2013.01); *G01N 2800/347* (2013.01); *G01N 2800/50* (2013.01); *G01N 2800/56* (2013.01)

KIDNEY DISEASE BIOMARKER

CROSS REFERENCE TO RELATED APPLICATIONS

This application is a U.S. National Stage Application filed under 35 U.S.C. § 371 and claims priority to International Application No. PCT/GB2013/052148, filed Aug. 12, 2013, which application claims priority to Great Britain Application No. GB 1214440.8, filed Aug. 13, 2012, the disclosure of which are incorporated herein by reference.

FIELD OF THE INVENTION

The present invention relates to renal disease and methods for its diagnosis.

BACKGROUND OF THE INVENTION

Renal disease is a general term, which describes a class of conditions in which the kidneys fail to filter and remove waste products from the blood. There are two forms of renal disease; acute kidney injury (AKI) and chronic kidney disease (CKD). CKD is usually asymptomatic, except in its most advanced state. Consequently, blood and/or urine tests generally are required to make a diagnosis.

The definition of CKD developed by the Kidney Disease Outcomes Quality Initiative (KDOQI) was:
  1. Kidney damage present for at least 3 months, as defined by structural or functional abnormalities (most often based on increased albuminuria e.g. urinary albumin/creatinine ratio [UACR]≥30 mg/g) and/or
  2. Glomerular filtration rate (GFR)<60 mL/min/1.73 $m^2$ present for at least 3 months.

Within this framework, KDOQI then classified CKD into five stages, as follows:
  Stage 1: Kidney damage with GFR 90 mL/min/1.73 $m^2$.
  Stage 2: Kidney damage with GFR 60-89 mL/min/1.73 $m^2$.
  Stage 3: GFR 30-59 mL/min/1.73 $m^2$.
  Stage 4: GFR 15-29 mL/min/1.73 $m^2$.
  Stage 5: GFR<15 mL/min/1.73 $m^2$ or kidney failure treated by dialysis or transplantation.

In the United States, based on data from the 1999-2006 National Health and Nutrition Examination Survey (NHANES) study, an estimated 11.1 percent (22.4 million) of adults aged 20 or older have CKD stages 1-3. An additional 0.8 million U.S. adults aged 20 or older have CKD stage 4, and more than 0.3 million have stage 5 CKD and receive hemodialysis.

Analyses of NHANES data between 1988-1994 and 1999-2004 suggest that the prevalence of CKD is rising for every CKD stage, but with a particular increase in the prevalence of individuals classified with CKD stage 3. The number of patients with stage 5 CKD requiring dialysis also has increased. It has been estimated that more than 700,000 individuals will have End Stage Renal Disease (ESRD) by 2015.

Although CKD can be caused by primary kidney disease (e.g. glomerular diseases, tubulointerstitial diseases, obstruction, and polycystic kidney disease), in the vast majority of patients with CKD, the kidney damage is associated with other medical conditions such as diabetes and hypertension. In 2008, excluding those with ESRD, 48 percent of Medicare patients with CKD had diabetes, 91 percent had hypertension, and 46 percent had atherosclerotic heart disease. Other risk factors for CKD include age, obesity, family history, and ethnicity.

CKD has been associated with numerous adverse health outcomes. Many studies have reported that a GFR of 30-59 mL/min/1.73 $m^2$ is associated with an increased risk of mortality, cardiovascular disease, fractures, bone loss, infections, cognitive impairment, and frailty. Similarly, there appears to be a graded relationship between the severity of proteinuria or albuminuria and adverse health outcomes, including mortality, ESRD, and cardiovascular disease. Further, the risk for adverse outcomes conferred by reduced GFR and increased albuminuria (or proteinuria) appears to be independent and multiplicative.

The rationale for considering screening for early-stage CKD includes the high and rising prevalence of CKD, its known risk factors, its numerous adverse health consequences, its long asymptomatic phase, the availability of potential screening tests for CKD, and the availability of treatments that may alter the course of early-stage CKD and reduce complications of early-stage CKD or its associated health conditions.

Some organizations already recommend CKD screening in selected populations. Kidney Disease: Improving Global Outcomes (KDIGO) recommends screening of all patients with hypertension, diabetes, or cardiovascular disease. The American Diabetes Association recommends annual screening of all adults with diabetes, based on "expert consensus or clinical experience." The Joint National Committee on Prevention, Detection, Evaluation, and Treatment of High Blood Pressure (JNC7) recommends annual screening of all patients with combined hypertension and diabetes. Also advocating selected screening, the National Kidney Foundation sponsors free CKD screening for all adults with hypertension, diabetes, or a primary relative with a history of kidney disease, hypertension, or diabetes.

In most patients with CKD stages 1-3 GFR declines slowly. However, the rate of decline varies among individuals, and many factors appear to impact progression. Because CKD stages 1-3 usually progress asymptomatically, detection of early-stage CKD requires laboratory testing.

Some organizations recommend monitoring for changes in kidney function or damage in patients with CKD. For example, the Kidney Disease Outcomes Quality Initiative (KDOQI) recommends at least annual estimated GFR measurement in adults with CKD in order to predict onset of ESRD and evaluate the effect of CKD treatments. JNC7 recommends annual quantitative measurement of albuminuria in all patients with "kidney disease." KDOQI also recommends more frequent monitoring of CKD patients with worsening kidney function.

The appearance in the blood of cellular proteins released after tissue injury is gaining more and more interest as being important in the management of patients with tissue injury due to acute ischemia/reperfusion, neurological disorders, cancer, organ rejection or trauma. Fatty acid-binding protein (FABP) is one such tissue injury biomarker. It is a relatively small cytoplasmic protein (15 kDa), which is abundantly expressed in tissues with an active fatty acid metabolism e.g. heart and liver. Nine distinct types of FABP have now been identified and each type exhibits a characteristic pattern of tissue distribution. They were named according to the tissue in which they were first discovered and include liver-type (L-FABP/FABP1), intestinal-type (I-FABP/FABP2), muscle and heart-type (H-FABP/FABP3), adipocyte-type (A-FABP/FABP4), epidermal-type (E-FABP/FABP5), ileal-type (I-FABP/FABP6), brain-type (B-FABP/FABP7), myelin-type (M-FABP/FABP8) and testis-type (T-FABP/FABP9).

FABPs bind long chain fatty acids (FA) with high affinity. Their tertiary structure incorporates a slightly elliptical beta-barrel linked to a helix-turn-helix motif, thought to act as a portal for FA access and egress. Their primary function is the facilitation of intracellular long-chain fatty acid transport, while other functions include regulation of gene expression by mediating fatty acid signal translocation to peroxisome proliferator activated receptors (PPARs).

FABP1 is expressed in the proximal tubules of the kidney, liver, intestine, pancreas, lung and stomach. It has been hypothesized to be involved in lipid absorption by the enterocyte and in hepatocyte lipid transport and lipoprotein metabolism. Its unique binding and surface characteristics are likely to contribute to its specific functional properties. In contrast to the stoichiometric binding of long-chain FA by other FABPs, each FABP1 molecule binds two FA molecules. It also binds a variety of other small hydrophobic ligands such as lysophospholipids, heme and vitamin K.

U.S. Pat. No. 7,592,148 B1 discloses a method for diagnosis or prognosis of kidney disease in humans, which comprises detecting FABP1 in kidney tissue or urine. Kamijo et al. (Diabetes Care 2011; 34:691-6) employed the CMIC ELISA to demonstrate that urinary excretion of FABP1 increases with the deterioration of renal function, while serum FABP1 was not significantly affected. These methods teach the determination of FABP1 in urine as the sample matrix. The CMIC ELISA is commercially available for urine analysis of FABP1. U.S. Pat. No. 7,592,148 B1 reports the analysis of 34 urine specimens, collected from patients with CKD. In addition, the amount of NAG (N-acetyl-$\beta$-D-glucosaminidase) in the urine specimens was also determined. NAG is a marker enzyme existing in kidney tissue cells and the level of NAG in urine is generally considered as an indicator for kidney tissue injury. It was confirmed that the level of NAG and that of FABP1 positively correlate with each other in standard cases. However, in 15% of cases, although the level of NAG was high, the level of FABP was low. It was suggested that, in this group, the level of FABP1 in kidney tissues is low. However, it might also be postulated that the low level of FABP1 in these samples may be due to the nature of the disease in these particular patients, which results in a reduction in the amount of FABP1 leaked into the urine.

There is scientific literature to suggest that the findings of the publication by Kamijo et al have not been consistent with work done by other groups. Kim S S et al. (Diab Res Clin Pract, 2012) found that FABP1 was not significantly elevated in the urine of patients with microalbuminuria. Furthermore they found that many of the urine samples were below the detectable cut off range of the CMIC ELISA used in the study. Kamijo et al (2006) indicate the use of serum FABP1 as not being an effective biomarker for kidney disease as the source of FABP1 can also originate from liver tissue damage. This would naturally lead others to ignoring the utility in measuring serum levels of FABP1 to aid the diagnosis of renal disease.

Despite the importance of measuring clinical parameters for CKD in serum or urine, there are few diagnostic tests to predict and monitor the progression of this disease. Measurement of GFR is not sufficiently sensitive for early detection of kidney disease, while the measurement of urinary protein is not specific for kidney disease, nor is it suitable for monitoring the progression of the disease. Therefore, there is a requirement for a specific and sensitive clinical marker for the diagnosis of early CKD and staging of renal disease.

SUMMARY OF THE INVENTION

The present invention provides methods for the diagnosis of renal dysfunction. More specifically the invention provides a simple blood test with high sensitivity and specificity for FABP1 which provides the means for an early diagnosis and staging of CKD.

The present invention is based on the surprising finding by the inventors that a progressive up-regulation of FABP1 is seen in serum from patients with stage 1, 2 and 3 CKD compared with serum from control individuals.

In a first aspect, a method of stratifying a patient suffering from CKD into one of stages 1-3 of CKD, comprising determining the level of the biomarkers FABP1, $\gamma$-GT, AST, creatinine and cystatin C in a sample obtained from the patient and comparing the level of FABP1 in the sample to a control value and the levels of $\gamma$-GT, AST, creatinine and cystatin C in the sample to a range of control values for each biomarker, wherein an increased level of FABP1 compared to the control value and levels of $\gamma$-GT, AST, creatinine and cystatin C within the range of control values for each biomarker indicate that the patient suffers from stage 1 CKD or wherein an increased level of FABP1 compared to the control value, levels of $\gamma$-GT and AST within the range of control values for each biomarker, and increased levels of creatinine and cystatin C compared to an upper threshold of the control range for these biomarkers indicate that the patient suffers from stage 2 or stage 3 CKD.

In a second aspect, the invention provides a method for determining whether a patient has, or is at risk of developing, renal dysfunction comprising determining the level of FABP1 in a sample isolated from the patient by contacting the sample with a solid state device comprising a substrate having an activated surface on to which is applied an antibody to FABP1 to discreet areas of the activated surface and comparing the level of FABP1 in the sample to a control value of FABP1, wherein an increase in FABP1 compared to the control value indicates the patient has, or is at risk of developing, renal dysfunction.

In a third aspect the invention is a solid state device comprising a substrate having an activated surface on to which is applied an antibody to FABP1 to discreet areas of the activated surface.

In a fourth aspect the invention is a method of determining the efficacy of a treatment for CKD, comprising stratifying a patient suffering from CKD into one of stages 1-3 of CKD according to the method of the first aspect of the present invention before and after treatment, wherein a reduction in the stage of CKD following treatment indicates that the treatment has been successful.

In a fifth aspect the invention is a method of stratifying a patient suffering from CKD into one of stages 1-3 of CKD to determine an appropriate treatment, comprising carrying out the method of the first aspect of the invention and determining the most appropriate treatment based on the stage of CKD into which the patient is classed.

DESCRIPTION OF THE DRAWINGS

The invention is described with reference to the following Tables and Figures in which.

Figure 4:
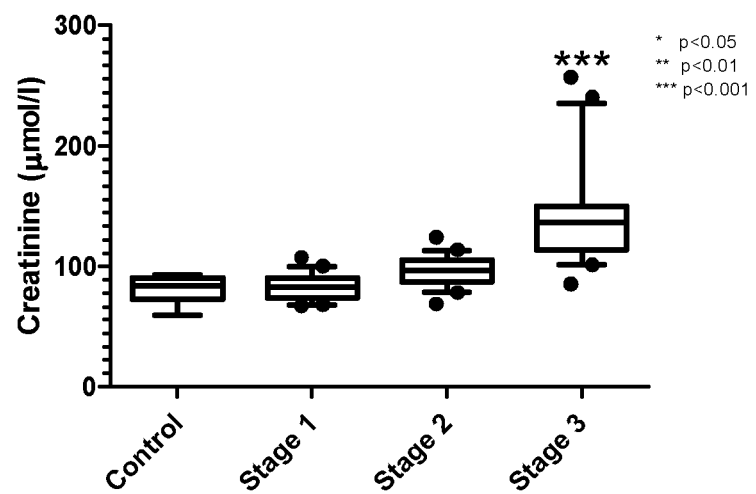
Figure 5:
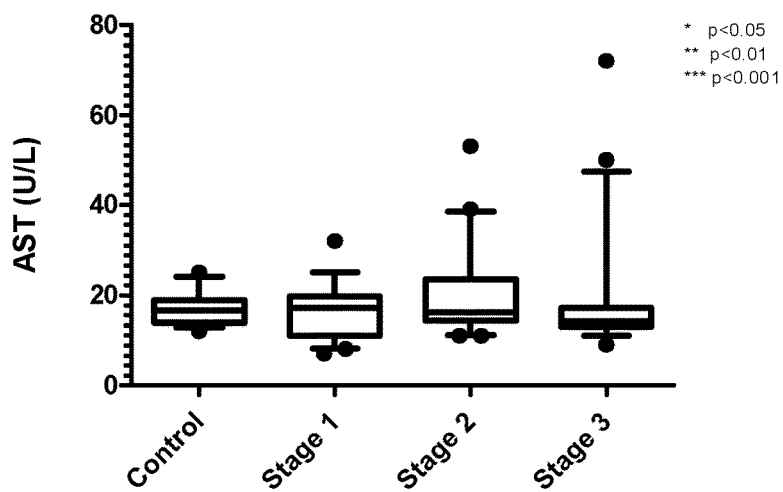
Figure 6:
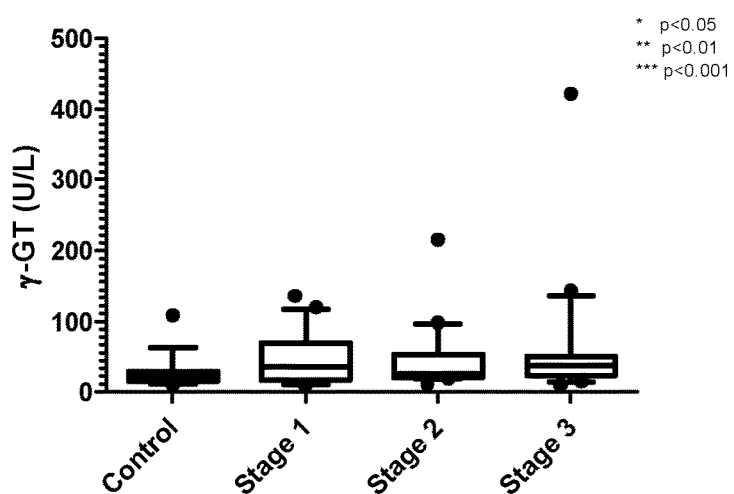
Figure 7:
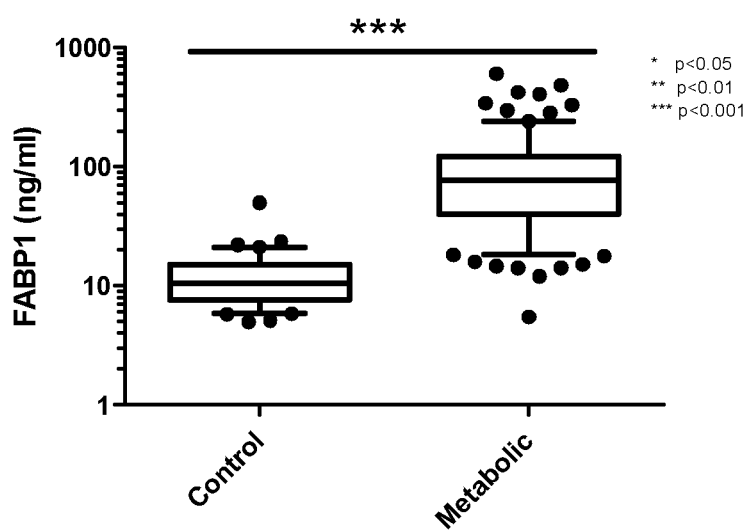
Figure 8:
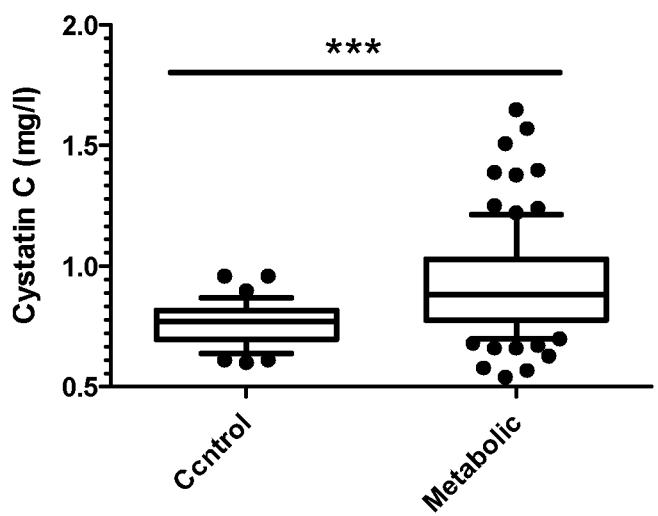
Figure 9:
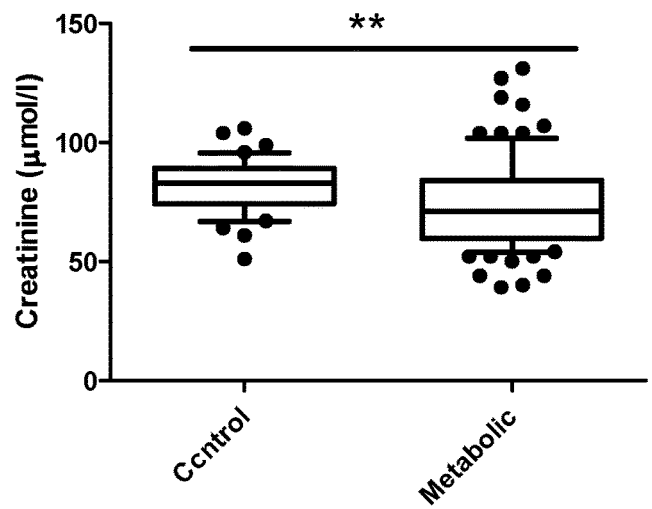
Figure 10:
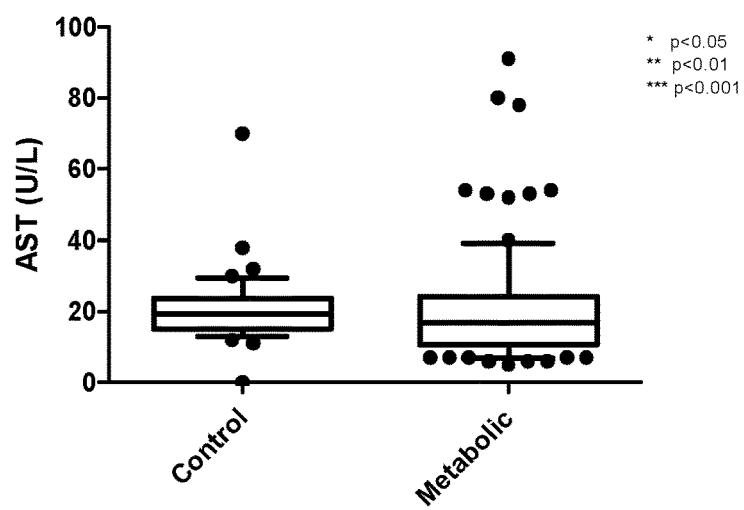
Figure 11:
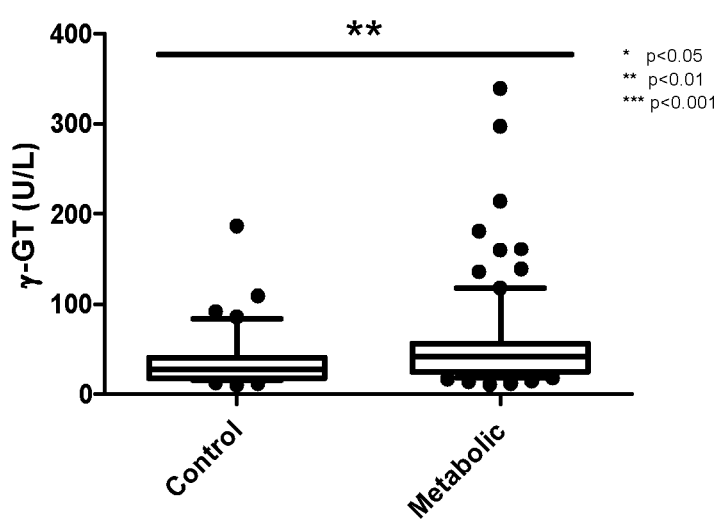

Table 5 and FIG. 4 show the levels of creatinine in serum from patients with renal disease;

FIG. 5 shows the level of AST in serum from patients with renal disease;

FIG. 6 shows the level of γ-GT in serum from patients with renal disease;

FIG. 7 shows the levels of FABP1 in serum taken from metabolic patients compared to controls;

FIG. 8 shows the levels of cystatin C in serum taken from metabolic syndrome patients compared to controls;

FIG. 9 shows the levels of creatinine in serum taken from metabolic syndrome patients compared to controls;

FIG. 10 shows the level of AST in serum samples from patients with metabolic syndrome and controls; and FIG. 11 shows the level of γ-GT in serum samples from patients with metabolic syndrome and controls.

Figure 12:
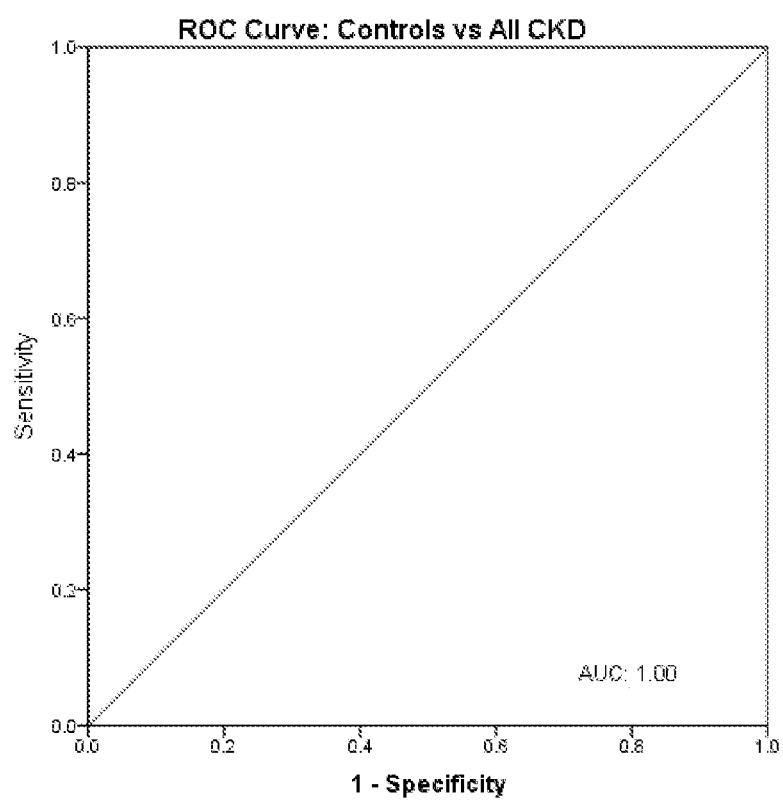

FIG. 12 shows a receiver-operator curve (ROC) analysis to determine the specificity and sensitivity for the invention to discriminate between control groups and all CKD patients.

Figure 13:
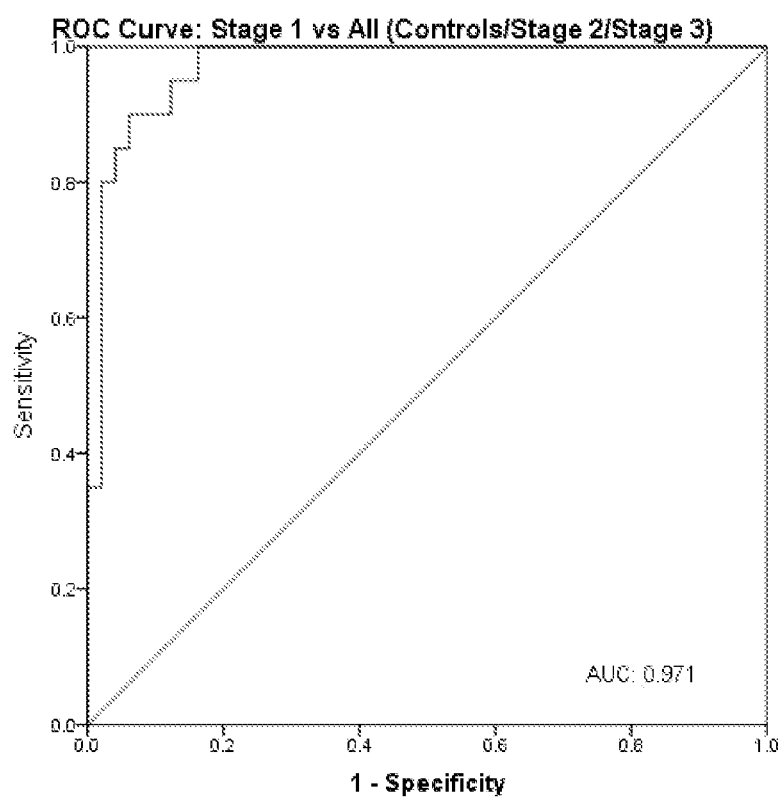

FIG. 13 shows a receiver-operator curve (ROC) analysis to determine the specificity and sensitivity for the invention to discriminate between Stage 1 CKD patients and all others including control groups and Stage 2 and Stage 3 CKD patients.

Figure 14:
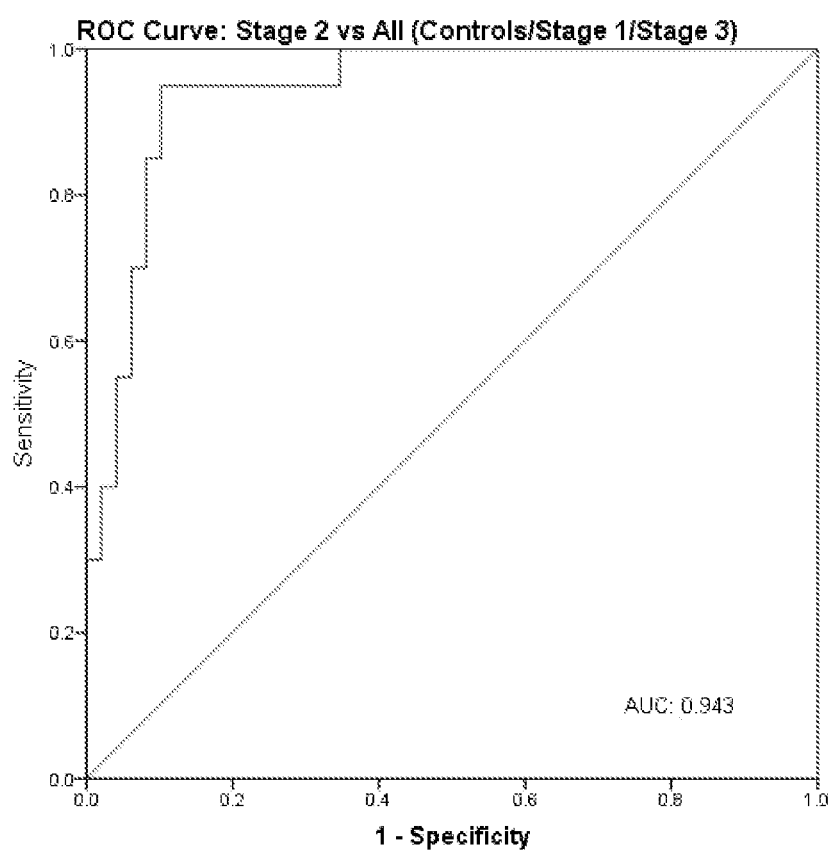

FIG. 14 shows a receiver-operator curve (ROC) analysis to determine the specificity and sensitivity for the invention to discriminate between Stage 2 CKD patients and all others including control groups and Stage 1 and Stage 3 CKD patients.

Figure 15:
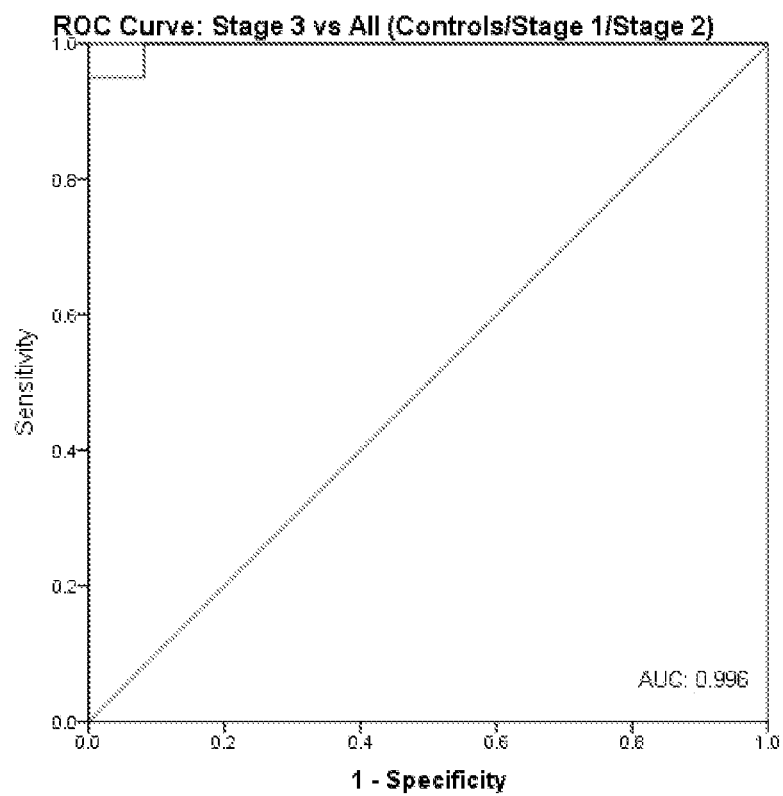

FIG. 15 shows a receiver-operator curve (ROC) analysis to determine the specificity and sensitivity for the invention to discriminate between Stage 3 CKD patients and all others including control groups and Stage 1 and Stage 2 CKD patients.

DETAILED DESCRIPTION OF THE INVENTION

The present invention provides a method for the detection of renal dysfunction by determining the level of FABP1 in a sample obtained from a patient and comparing the level of FABP1 with a control. An increased level of FABP1 in the sample compared to the control indicates that the patient suffers from, or is at risk of developing, renal dysfunction.

The term "renal dysfunction" in the context of the present invention is understood to mean conditions or diseases characterised by a decrease in renal function compared to healthy patients. Renal diseases may include chronic kidney disease (CKD), acute kidney injury (AKI), diabetic nephropathy, glomerulonephritis, focal glomerulosclerosis, immune complex nephropathy or lupus nephritis. Renal dysfunction may be caused by drug-induced renal injury or kidney graft rejection. Renal dysfunction may be characterised as nephrotic syndrome or renal insufficiency.

In the context of the present invention, a "control value" is understood to be the level of a particular biomarker, such as FABP1, γ-GT, AST, creatinine or cystatin C typically found in healthy individuals. The control level of a biomarker may be determined by analysis of a sample isolated from a healthy individual or may be the level of the biomarker understood by the skilled person to be typical for a healthy individual. The "control value" may be a range of values considered by the skilled person to be a normal level for the biomarker in a healthy individual. The skilled person would appreciate that control values for a biomarker may be calculated by the user analysing the level of the biomarker in a sample from a healthy individual or by reference to typical values provided by the manufacturer of the assay used to determine the level of the biomarker in the sample.

Preferably the sample isolated from the patient is a serum sample, but may also be plasma. The determination of the level of FABP1 may be done on one or more samples from the patient. The sample may be obtained from the patient by methods routinely used in the art.

The present inventors have found that there is a stepwise increase in FABP1 in samples obtained from patients suffering from CKD which correlates with the stage of progression of the disease. Thus, the present invention may be used to diagnose early stage CKD. In the context of the present invention, "early stage" is understood to mean any of the first to third stages of CKD as defined by the KDOQI classification.

In a further aspect, the present invention provides a method of classifying patients at the various stages of CKD according to the level of FABP1 in the sample and comparing that level with the level of FABP1 of a control range of values having an upper and lower threshold level. The control range of values of FABP1 may vary dependent on demographic of population and the sample being tested. For example, the control range of values from a healthy individual may vary from a blood sample compared to a urine sample. The upper and lower threshold for a given sample and patient demographic may be determined by the skilled person by analyzing samples from a patient cohort to find average values. An example of such a method is described in Example 7. In the context of a serum sample, preferably, the level of FABP1 in the serum from approximately 15 ng/ml to 76 ng/ml for females and from approximately 21 ng/ml to 151 ng/ml for males indicates stage 1 or stage 2 CKD. A concentration of FABP 1 above approximately 75 ng/ml for females or above approximately 152 ng/ml for males indicates stage 3 CKD or above. The stepwise increase in serum FABP1 levels means that it is possible to assess the rate of progression of renal disease in a patient.

The stratification of patients as in one of the stages of CKD is useful to assess whether a patient would benefit from one treatment type compared to another and also to monitor whether a treatment is successful. Stratification of patients also assists in determining the prognosis of the patient thereby enabling future care requirements.

Estimated GFR is inversely correlated to creatinine and/or cystatin C levels. An increase in creatinine or cystatin C levels compared to a control value in patients presenting with increased levels of FABP1 allow the patients to be stratified as stage 1 or stage 2 CKD. Thus, the method of the invention may further comprise a determination of the level of creatinine and/or cystatin C in the sample and comparing the level with the normal ranges (Table 13). Patients having increased levels of FABP1 compared to a control value (as demonstrated in Example 7) but levels of creatinine and cystatin C within the control ranges of these biomarkers may be classed as stage 1 CKD. Patients having increased levels of FABP1 compared to a control value and increased levels of creatinine and/or cystatin C compared to a range of control values for each biomarker may be classed as stage 2 CKD. An increased level of FABP1 above a control range and increased levels of creatinine and/or cystatin C compared to a range of control values for each biomarker indicate the patient suffers from stage 3 CKD or above. Levels of γ-GT, AST, creatinine and cystatin C can be determined through routinely used quantitative methods known to the art. Thus, the methods of the present invention allow the stratification of a patient having renal dysfunction as a non-CKD patient or a patient at one of the stage 1 to 3 of CKD. Preferably, the stratification of the patient may follow the criteria:

"Non-CKD"—FABP1 less than lower threshold calculated by the skilled person from a cohort of healthy individuals. Preferably, this lower threshold is (Female) 15 ng/ml and (Male) 21 ng/ml;

"Stage 1"—FABP1 above a lower threshold defined above and creatinine and cystatin C level within the control range for these biomarkers and AST or γ-GT within the control range for these biomarkers;

"Stage 2"—FABP1 above lower threshold as defined above and creatinine and/or cystatin C level above the control range for these biomarkers;

"Stage 3"—FABP1 above the higher threshold and creatinine and/or cystatin C higher than the control range for these biomarkers. Preferably the higher threshold for FABP1 levels is (Female)>75 ng/ml and (Male)>151 ng/ml.

The control range and upper threshold levels for the biomarkers cystatin C, creatinine, AST and γ-GT are given in Tables 4-6, respectively.

The methods of the present invention may use methods for determining the level of FABP1, γ-GT, AST, cystatin C and creatinine known in the art, such as enzymatic and/or chemical protein determination or immunological assay based methods. Immunological assays for determining the level of FABP1, γ-GT, AST, cystatin C and creatinine can be performed in a variety of assay formats, including sandwich assays e.g. (ELISA), competition assays (competitive RIA), bridge immunoassays, immunohistochemistry (IHC) and immunocytochemistry (ICC). Methods for determining the level of FABP1, γ-GT, AST, cystatin C and creatinine include contacting a patient sample with antibodies that binds to FABP1, γ-GT, AST, cystatin C and creatinine and detecting binding. Antibodies having specificity for FABP1, γ-GT, AST, cystatin C and creatinine can be immobilised on a support material using conventional methods. Binding of FABP1, γ-GT, AST, cystatin C and creatinine to the antibodies on the support can be detected using further antibodies having specificity for FABP1, γ-GT, AST, cystatin C and creatinine or using physical methods such as surface plasmon resonance (Biacore Int, Sweden).

Preferably, a solid state device may be used to determine the level of FABP1 in the sample isolated from the patient. The solid state device comprises a substrate having an activated surface on to which is applied an antibody to FABP1 to discreet areas of the activated surface. Preferably the solid state device may perform multi-analyte assays such that the level of FABP1 in a sample isolated from the patient may be determined simultaneously with the level of any one of aspartate transaminase (AST) and gamma glutamyl transpeptidase (γ-GT), cystatin C and creatinine in the sample. In this embodiment, the solid state device has a multiplicity of discrete reaction sites each bearing a desired antibody covalently bound to the substrate, and in which the surface of the substrate between the reaction sites is inert with respect to the target biomarker. The solid state, multi-analyte device used in the present invention may therefore exhibit little or no non-specific binding.

A device that may be used in the invention may be prepared by activating the surface of a suitable substrate, and applying an array of antibodies on to discrete sites on the surface. If desired, the other active areas may be blocked. The ligands may be bound to the substrate via a linker. In particular, it is preferred that the activated surface is reacted successively with an organosilane, a bifunctional linker and the antibody. The solid state device used in the methods of the present invention may be manufactured according to the method disclosed in, for example, GB-A-2324866 the contents of which is incorporated herein in its entirety. Preferably, the solid state device used in the methods of the present invention is the Biochip Array Technology system (BAT) (available from Randox Laboratories Limited).

The solid state device used in the method of the present invention comprises an antibody to FABP1. Preferably the antibody is specific for FABP1 and exhibits a cross reactivity of less than 0.5%, preferably less than 0.1%, to other FABP subtypes and myoglobin. Preferably, the FABP1 antibody is a monoclonal antibody.

An increase in serum FABP1 has also been shown to be caused by liver disease. In order to discriminate between an increase in FABP1 levels being caused by renal disease and liver disease the present invention may further comprise the determination of one or more biomarkers of liver disease and comparison of the level of these biomarkers with controls. The biomarkers of liver disease may include AST and γ-GT. Thus, an observed increase in the level of FABP1 in the sample may be validated as the patient having renal disease by confirming that other liver damage markers, such as AST or γ-GT, are within normal ranges to ensure the accuracy of the test. Thus, in the case of discriminating between increased levels of FABP 1 caused by liver disease or kidney disease and to stratify patients between stage 1 CKD and stage 2 CKD, the solid state device used in the method of the present invention may further comprise antibodies specific to AST, γ-GT, cystatin C and creatinine.

The methods of the present invention may be used to monitor a patient post-operatively to assess the risk of them developing renal complications. Specifically, a sample may be obtained from a patient at given intervals post operatively and the level of FABP1 in the sample determined. An assessment of the level of FABP1 over a particular time frame provides the clinician with an indication of whether the patient is suffering early stage CKD and medical intervention can be taken accordingly.

It is accepted that patients with metabolic syndrome are at an increased risk of developing CKD. Therefore an assay that can identify and stratify these patients into the various stages of CKD would be of significant clinical benefit to assess the likely success of a given treatment on the patient or to provide prognostic guidance for future treatment protocols. The criteria for the diagnosis of metabolic syndrome according to the International Diabetes Federation are as follows:

| Central obesity (defined as waist circumference* with ethnicity specific values) plus any two of the following four factors: | |
|---|---|
| Raised triglycerides | >/=150 mg/dL (1.7 mmol/L) or specific treatment for this lipid abnormality |
| Reduced HDL cholesterol | <40 mg/dL (1.03 mmol/L) in males <50 mg/dL (1.29 mmol/L) in females or specific treatment for this lipid abnormality |
| Raised blood pressure | systolic BP >/=130 or diastolic BP >/=85 mmHg or treatment of previously diagnosed hypertension |
| Raised fasting plasma glucose | (FPG) >/=100 mg/dL (5.6 mmol/L) or previously diagnosed type 2 diabetes If above 5.6 mmol/L or 100 mg/dL, OGTT is strongly recommended but is not necessary to define presence of the syndrome. |

*If BMI is >30 kg/m2, central obesity can be assumed and waist circumference does not have to be measured.

The inventors have found that the FABP1 serum analysis of metabolic syndrome patients show a statistically significant increase in the concentration of FABP1 compared to healthy donor samples. The method of the present invention is therefore particularly suited to patients presenting with metabolic syndrome as a means of stratifying these patients into the various stages of CKD. More preferably, the patient suffering from metabolic syndrome may be diagnosed by the method of the invention during early stages of CKD (including stages 1 or 2) and be clinically managed and monitored to decrease the risk of developing renal disease. Equally, metabolic syndrome patients with compromised GFR can be further stratified using the method of the present invention to identify the patients who are at greater risk of renal disease.

Patients suffering from metabolic syndrome may have increased levels of FABP1 due to underlying liver disease. Therefore, when the patient suffers from metabolic syndrome, the method of the invention may further comprise the step of determining the level of biomarkers for liver disease in a sample obtained from the patient, such as AST or γ-GT, and comparing the level of these markers to a control to validate that the increase in FABP1 is due to kidney disease.

The invention is further described with reference to the following non-limiting examples:

Example 1: Expression of Recombinant Human FABP1

Human FABP-1 Antigen Expression in *E. coli* (BL21) Cells

The FABP-1 expression construct, under the control of a T7 promoter was transformed into *E. coli* K12 strain BL21 cells. Transformed cells were grown overnight on LB agar plates containing 100 μg/ml ampicillin. An overnight culture was grown from a freshly streaked plate and used to inoculate 100 ml of LB broth. The culture was incubated at 37° C. until the cell density reached an $OD_{600}$ between 0.4-0.8 AU. Expression by T7 RNA polymerase was induced by the addition of 1 mM IPTG and the cells were incubated for 2 hours at 37° C. with shaking.

Human FABP-1 Antigen Purification

Cells were harvested by centrifugation (15 min; 5000 rpm; 4° C.) and the pellets washed in 1'PBS pH 7.2. Pellets were then snap frozen in liquid nitrogen. The cell pellet was lysed in CelLytic B (Sigma) containing 2 mM PMSF (Sigma) and 10 μg/ml DNAse I (Sigma) for 1 hour at 4° C. with mixing. The supernatant was then clarified by centrifugation (15 min; 5000 rpm; 4° C.). A calibrated cobalt-sepharose column (capacity 10 mg HIS tagged protein/ml resin) was prepared and washed with 20 mM Tris HCl pH 8.0 (5 CV). The HIS tagged protein was purified by gravity-flow and then desalted on a PD-10 column into 1×PBS pH 7.2. The concentration of the protein was determined by $A_{280}$. Purity was determined by SDS PAGE—silver staining and QuantiScan©.

Example 2: Development of Monoclonal Antibodies Specific to FABP1

An aqueous solution of recombinant human FABP1 was formulated with Freund's Complete Adjuvant (FCA) to form an emulsion consisting of 0.1 mg/ml immunogen in 50% (v/v) FCA. Three sheep were immunized with this emulsion, 0.25 ml being intramuscularly injected at each of four sites in the flank of each animal. Subsequent immunizations (boosts) were composed of 0.05 mg/ml of immunogen, emulsified in 50% (v/v) Freund's Incomplete Adjuvant (FIA), and these were administered in the same manner on a monthly basis until a polyclonal response was confirmed. Lymph nodes were then harvested following the subcutaneous immunization of a further two boosts in the axillary and prescapular regions of each animal.

The harvested lymph nodes were perfused with media and dissected using scissors and forceps to isolate lymphocytes. Fusion of the isolated lymphocytes with a heteromyeloma cell-line was carried out at a ratio of approximately 2:1 by addition of polyethylene glycol 1500 (PEG). The resulting fusions were transferred into 7×96 well plates in 20% DMEM P/S, with ×1 hypoxanthine-aminopterin-thymidine (HAT). On Day 7, media was replenished on each fusion plate with 20% DMEM P/S, with ×1 HAT, and on Day 14, 180 μl/well of supernatant was removed and used to screen the hybridoma culture supernatants by ELISA. Hybridomas exhibiting specificity for FABP1 were selected.

Positive hybridomas were cloned to produce stable monoclonal hybridomas using 1% methylcellulose at 37° C., 5% CO2. Two cell lines, P2386 and P2388, were identified as meeting specifications and were cloned in triplicate before being cloned by limit dilution.

Example 3: Characterisation of FABP1 Monoclonal Antibodies

Purified monoclonal antibodies from hybridomas P2386 and P2388 (see above) were then assessed in direct binding assays with these FABP family recombinant proteins using 1 μg/ml of monoclonal and a titration of each variant of FABP in order to confirm specificity. Results are shown in Table 1 below.

Further analytical evaluation showed that the monoclonal antibodies were specific for FABP1, exhibiting a combined cross-reactivity of <0.1% for FABP2, FABP3, FABP4, FABP5, FABP6, FABP7, FABP8, FABP9 and myoglobin. These results are presented below in Table 2.

TABLE 1

| Supplier | Cat # | ng/ml | 1582.28 | 500.72 | 158.46 | 50.14 | 15.87 | 5.02 | 1.59 | 0.50 | 0.16 | 0.05 | 0 |
|---|---|---|---|---|---|---|---|---|---|---|---|---|---|
| | | | P2386 @ 1 μg/ml MAP-DAS-094 @ 1:5K | | | | | | | | | | |
| BioVendor | RD172240100 | FABP-Liver | 2.498 | 2.283 | 1.770 | 1.170 | 0.650 | 0.325 | 0.204 | 0.198 | 0.130 | 0.089 | 0.065 |
| R&D systems | 2694-CL/CF | FABP-Recombinant | 0.062 | 0.063 | 0.054 | 0.070 | 0.059 | 0.051 | 0.061 | 0.064 | 0.056 | 0.067 | 0.061 |
| Capricorn | FAB-063 | FABP-Cardiac | 0.088 | 0.068 | 0.056 | 0.069 | 0.078 | 0.047 | 0.057 | 0.054 | 0.066 | 0.063 | 0.062 |
| BioVendor | RD172036100 | FABP-Adipose | 0.059 | 0.059 | 0.055 | 0.070 | 0.058 | 0.057 | 0.062 | 0.053 | 0.063 | 0.067 | 0.058 |
| BioVendor | RD172036100 | FABP-Epidermal | 0.065 | 0.062 | 0.059 | 0.071 | 0.061 | 0.056 | 0.065 | 0.071 | 0.068 | 0.054 | 0.057 |
| Randox | PAS10094 | FABP-Ileal | 0.064 | 0.063 | 0.056 | 0.068 | 0.057 | 0.057 | 0.064 | 0.062 | 0.060 | 0.065 | 0.058 |
| Abnova | H00002173-P01 | FABP-Brain | 0.076 | 0.064 | 0.054 | 0.068 | 0.062 | 0.048 | 0.067 | 0.062 | 0.066 | 0.062 | 0.059 |
| Randox | PAS10092 | FABP-Myelin | 0.092 | 0.062 | 0.059 | 0.079 | 0.068 | 0.054 | 0.048 | 0.067 | 0.061 | 0.071 | 0.053 |
| | | | P2388 @ 1 μg/ml MAP-DAS-094 @ 1:5K | | | | | | | | | | |
| BioVendor | RD172240100 | FABP-Liver | 2.639 | 2.406 | 1.976 | 1.357 | 0.738 | 0.334 | 0.168 | 0.148 | 0.115 | 0.106 | 0.055 |
| R&D systems | 2694-CL/CF | FABP-Recombinant | 0.067 | 0.061 | 0.062 | 0.060 | 0.055 | 0.067 | 0.047 | 0.049 | 0.056 | 0.056 | 0.054 |
| Capricorn | FAB-063 | FABP-Cardiac | 0.062 | 0.055 | 0.063 | 0.057 | 0.053 | 0.077 | 0.049 | 0.046 | 0.052 | 0.056 | 0.050 |
| BioVendor | RD172036100 | FABP-Adipose | 0.064 | 0.058 | 0.058 | 0.061 | 0.054 | 0.055 | 0.059 | 0.049 | 0.055 | 0.053 | 0.048 |

TABLE 1-continued

| Supplier | Cat # | | ng/ml | 1582.28 | 500.72 | 158.46 | 50.14 | 15.87 | 5.02 | 1.59 | 0.50 | 0.16 | 0.05 | 0 |
|---|---|---|---|---|---|---|---|---|---|---|---|---|---|---|
| BioVendor | RD172036100 | FABP-Epidermal | | 0.066 | 0.053 | 0.057 | 0.066 | 0.055 | 0.056 | 0.059 | 0.055 | 0.065 | 0.057 | 0.049 |
| Randox | PAS10094 | FABP-Ileal | | 0.066 | 0.054 | 0.056 | 0.056 | 0.059 | 0.054 | 0.059 | 0.054 | 0.057 | 0.052 | 0.049 |
| Abnova | H00002173-P01 | FABP-Brain | | 0.061 | 0.052 | 0.052 | 0.057 | 0.060 | 0.052 | 0.049 | 0.055 | 0.064 | 0.061 | 0.055 |
| Randox | PAS10092 | FABP-Myelin | | 0.079 | 0.075 | 0.064 | 0.075 | 0.061 | 0.058 | 0.066 | 0.069 | 0.062 | 0.069 | 0.059 |

TABLE 2

| Cross-Reactant | Concentration (ng/ml) | % Cross-reactivity |
|---|---|---|
| FABP2 | 4000 | 0.03 |
| FABP3 | 4000 | 0.07 |
| FABP4 | 4000 | 0.02 |
| FABP5 | 4000 | 0.03 |
| FABP6 | 4000 | 0.06 |
| FABP7 | 4000 | 0.03 |
| FABP8 | 4000 | 0.05 |
| FABP9 | 4000 | 0.07 |
| Myoglobin | 800 | 0.02 |

Example 4: Optimisation and Validation of FABP1 Assay

The characterised FABP1 monoclonal antibodies were employed in the development of a biochip sandwich immunoassay. The assay was applied to the Evidence Investigator analyser (available from Randox Laboratories), which utilises biochip array technology, based on ELISA immunoassay principles.

Epitope mapping of capture and detector/tracer antibodies was completed using overlapping peptides derived from FABP1 and established that the capture and detector/tracer antibodies bind to N- and C-terminal regions of FABP1 respectively. Biochip based immunoassays were employed to evaluate the analytical performance of the antibody pair, the assay was applied to the Evidence Investigator analyser. The FABP1 assay showed a sensitivity value of 0.66 ng/ml with an assay range of 0-400 ng/ml.

Prior to spotting, the biochip surface was activated as described in Fitzgerald S. P. et al, Clin. Chem. 51(7); 1165-1176; 2005. 10 nl capture antibody was spotted at 0.32 mg/ml in carbonate buffer, pH 9.6. The spotted biochips were blocked with 2% casein in carbonate buffer for one hour at room temperature and then washed with PBS. They were then stabilised, dried at 37° C., chopped and assembled into carriers, before being vacuum-sealed for storage at 2-4° C.

The samples were all assayed for FABP1, cystatin C, creatinine, AST and γ-GT.

Figure 1:
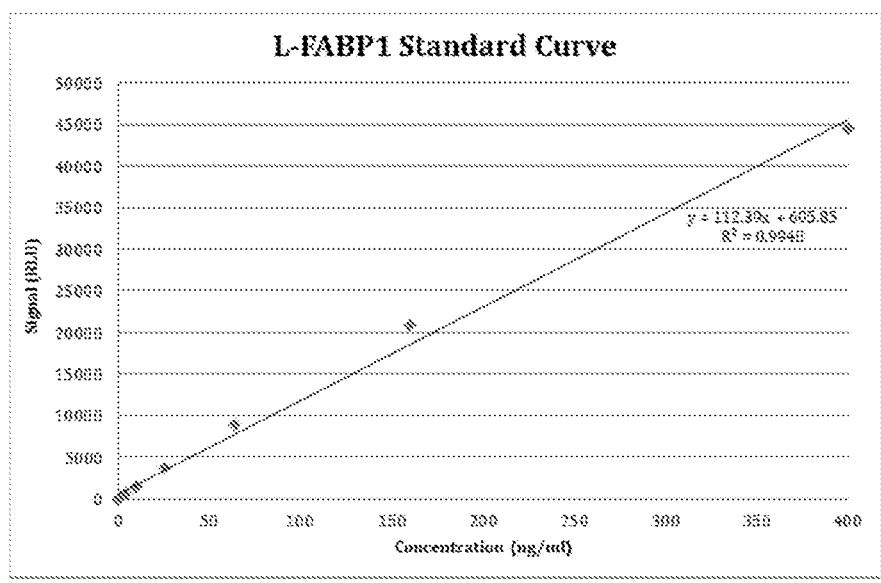
FIG. 1 shows FABP1 assay linearity.
Figure 2:
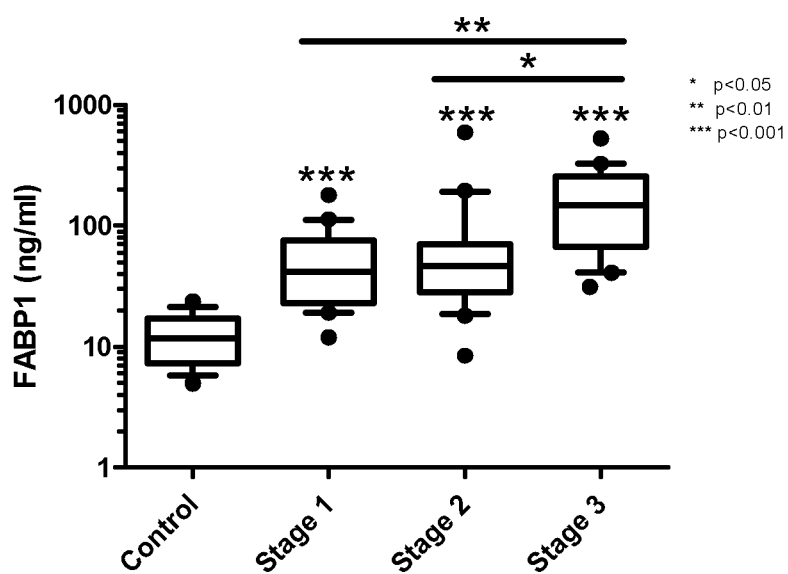
FIG. 2 shows FABP1 levels in serum from patients with renal disease.

These samples, along with serum from healthy donors, were assayed using the described invention for determining FABP1 concentration in a blood-based matrix. The levels of FABP1 measured by the assay in the renal disease patient's samples were compared to levels of FABP1 in the samples taken from healthy donors. Significance of results was determined using a Kruskal-Wallis (J American Stat Assoc 1952; 47:583-621) test followed by post hoc Mann-Whitney (Ann Math Stats 1947; 18:50-60) comparisons (corrected using Bonferonni's method (Pubblicazioni del R Istituto Superiore di Scienze Economiche e Commerciali di Firenze 1936; 8:3-62). The results demonstrated that the described invention was able to identify renal disease patients in all stages of disease. Levels of FABP1 were significantly increased in Stage 1 ($p<0.001$, n=20), Stage 2 ($p<0.001$, n=20) and Stage 3 ($p<0.001$, n=20) patients compared to the control group (n=9). Furthermore, serum from Stage 3 renal disease patients contained higher levels of FABP1 compared to Stage 1 ($p<0.01$, n=20) and Stage 2 ($p<0.05$, n=20) renal disease patients, with no significant difference between Stage 1 and Stage 2 patients observed. The results are shown below in Table 3 and in FIG. 2.

TABLE 3

| | FABP1 (ng/ml) | | | |
|---|---|---|---|---|
| | Control | Stage 1 | Stage 2 | Stage 3 |
| Median | 10 | 41.45 | 46 | 147.2 |
| Min | 3.6 | 11.9 | 8.4 | 31 |
| Max | 19.6 | 178.3 | 586.9 | 522.5 |
| Range | 3.6-19.6 | 11.9-178.3 | 8.4-586.9 | 31-522.5 |
| n = | 9 | 20 | 20 | 20 |
| p value (corrected) | | <0.001 | <0.001 | <0.001 |

This assay also demonstrated greater sensitivity for diagnosing renal disease at an early stage compared to other markers for kidney damage. This was The assay for FABP1 was designed to be specific for FABP1. The assay's specificity was evaluated by assessing cross-reactivity to panel of FABP proteins and related analytes (Table 2). For each of the panel analytes, 4000 ng/ml of the analyte was added to the calibration serum. This is equivalent to 10 times the upper level of quantification for FABP1. Myoglobin, a related analyte but not an FABP, was introduced at a concentration of 800 ng/ml. No significant cross-reactivity was observed with any of the cross-reactants. These data validate that the assay is specific for FABP1. The FABP1 assay specificity was evaluated by testing for non-specific binding of the conjugate with non-target assay components. The FABP1 conjugate was tested against the other panel components H-FABP3, B-FABP7 and M-FABP8. The L-FABP1 conjugate was run against each of the other panel components antigens and capture antibodies.

Example 5: Expression of FABP1 in Serum from Patients with Renal Disease

Serum samples were obtained from patients who have been classified as Stage 1, Stage 2 or Stage 3 using the method of classification detailed above. Specifically, the CKD sample cohort studied consisted of serum samples from male and female patients over 55 years old and included Stage 1, 2 and 3 CKD samples as defined by clinical guidelines.

Estimated glomerular filtration rate (EGFR) was determined according to the following formula described by Levey et al (Ann Intern Med 1999; 130(6):461-70):

$$EGFR = 186 \times (creatinine/88.4)^{-1.154} \times (Age)^{-0.203} \times [(0.742 \text{ if Female}) \times (1.210 \text{ if Black})];$$

where creatinine is measured in micromoles/liter.

Figure 3:
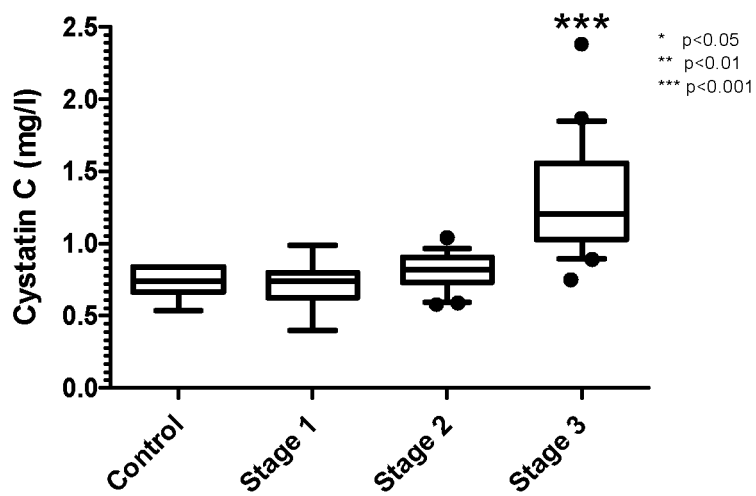
FIG. 3 shows the levels of cystatin C in serum from patients with renal disease.

The CKD sample cohort was composed of:
69 serum samples in total (33 male 36 female)
  20 CKD stage 1 patients (mean age 63 yrs)
  20 CKD stage 2 patients (mean age 66 yrs)
  20 CKD stage 3 patients (mean age 72 yrs)
  9 donor controls (mean age 59 yrs) demonstrated by analysing serum samples from Stage 1, Stage 2 and Stage 3 renal disease patients, as well as samples taken from healthy donors, for creatinine and cystatin C using the RX Daytona analyser (Randox, UK). Levels of these markers were determined and compared to control levels. There was no significant change in either cystatin C or creatinine in Stage 1 or Stage 2 Renal disease compared to the control group. However, both cystatin C and creatinine levels were significantly elevated in the Stage 3 renal disease group compared to controls. These data are shown in Tables 4 and 5 below and in FIGS. 3 and 4. These comparisons were based on the levels of the analytes and not whether they were above or below the normal range suggested by the instructions for use supplied by the manufacturer. Comparison between disease and control groups was used to simply identify markers which may be of interest at specific stages of disease and not to classify patients. These data suggest that the described invention acts as an early indicator for renal disease diagnosis and outperforms current techniques known in the art for diagnosis of renal dysfunction.

TABLE 4

Cystatin C (mg/l)

|  | Control | Stage 1 | Stage 2 | Stage 3 |
|---|---|---|---|---|
| Median | 0.74 | 0.74 | 0.82 | 1.21 |
| Min | 0.54 | 0.4 | 0.58 | 0.75 |
| Max | 0.84 | 0.99 | 1.04 | 2.38 |
| Range | 0.54-0.84 | 0.4-0.99 | 0.58-1.04 | 0.75-2.38 |
| n = | 9 | 19 | 20 | 20 |
| p value (Corrected) |  | 0.99 | 0.123 | <0.001 |

TABLE 5

Creatinine (umol/l)

|  | Control | Stage 1 | Stage 2 | Stage 3 |
|---|---|---|---|---|
| Median | 84.55 | 82.94 | 97.1 | 137.2 |
| Min | 59.55 | 67.72 | 69.23 | 85.26 |
| Max | 93.42 | 107.5 | 124.4 | 257.2 |
| Range | 59.55-93.42 | 67.72-107.5 | 69.23-124.4 | 85.26-257.2 |
| n = | 9 | 20 | 20 | 20 |
| p value (Corrected) |  | 0.96 | 0.078 | <0.001 |

It has been previously argued that serum levels of FABP1 have limited utility in diagnosing renal disease due to FABP1 also being produced in response to liver disease. To overcome this potential problem, serum samples from the renal disease and control groups were analysed using the RX Imola analyser (Randox, UK) for levels of known indicators of liver damage, AST and γ-GT. Both AST and γ-GT demonstrated no significant correlation with FABP1 in the renal disease and control groups. Furthermore, there was no significant change in either level of AST or γ-GT in patients diagnosed with either Stage 1, Stage 2 or Stage 3 CKD compared to control. These data are shown in Tables 6 and 7 below and in FIGS. 5 and 6. These data further emphasise the utility of serum FABP1 for the diagnosis of renal disease.

TABLE 6

AST (U/L)

|  | Control | Stage 1 | Stage 2 | Stage 3 |
|---|---|---|---|---|
| Median | 17 | 17 | 16 | 14 |
| Min | 13 | 7 | 11 | 9 |
| Max | 22 | 32 | 53 | 72 |
| Range | 13-22 | 7-32 | 11-53 | 9-72 |
| n = | 9 | 20 | 20 | 20 |
| p value (Corrected) |  | 1 | 1 | 0.8 |

TABLE 7 gamma-GT (U/L)

|  | Control | Stage 1 | Stage 2 | Stage 3 |
|---|---|---|---|---|
| Median | 24 | 36 | 26.5 | 37.5 |
| Min | 10 | 9 | 11 | 10 |
| Max | 109 | 136 | 216 | 422 |
| Range | 10-109 | 9-136 | 11-216 | 10-422 |
| n = | 9 | 20 | 20 | 20 |
| p value (Corrected) |  | 1 | 1 | 0.93 |

Example 6: Expression of FABP1 in Serum from Patients with Metabolic Syndrome

Serum samples were obtained from patients who have been classified as suffering from metabolic syndrome using the method of classification detailed above. These samples, along with serum from healthy donors, were assayed using the described invention for determining FABP1 concentration in a blood-based matrix. The levels of FABP1 measured by the assay in the metabolic syndrome patient samples were compared to levels of FABP1 in the samples taken from healthy donors. Significance of the results was determined using a Mann-Whitney test. The results demonstrated that the described invention was able to identify patients with metabolic syndrome compared to control groups. Serum taken from metabolic patients contained significantly higher levels of FABP1 ($p<0.001$, n=90) than found in healthy controls (n=40; Table 8)

Samples from metabolic syndrome patients and healthy volunteers were also measured for concentration of markers of kidney dysfunction. Serum concentration of cystatin C were significantly increased in the metabolic syndrome group compared to that of healthy volunteers ($p<0.001$, n=90, Table 9).

TABLE 8

FABP1 (ng/ml)

|  | Control | Metabolic |
|---|---|---|
| Median | 10.53 | 77.19 |
| Min | 4.97 | 5.48 |
| Max | 49.78 | 603.1 |
| Range | 4.97-49.78 | 5.48-603.1 |
| n = | 40 | 90 |
| p value |  | <0.001 |

TABLE 9

| Cystatin C (mg/L) | | |
|---|---|---|
| | Control | Metabolic |
| Median | 0.775 | 0.885 |
| Min | 0.6 | 0.54 |
| Max | 0.96 | 1.65 |
| Range | 0.6-0.96 | 0.54-1.65 |
| n = | 40 | 90 |
| p value | | <0.0001 |

Interestingly, levels of creatinine were reduced significantly compared to the control group (p<0.001, n=90, Table 10). Reduced creatinine levels can be an indication of reduced liver function, due to damage, therefore this highlights that other factors must be taken into consideration to rule out/rule in potential liver disease as concomitant pathology.

TABLE 10

| Creatinine (umol/l) | | |
|---|---|---|
| | Control | Metabolic |
| Median | 83 | 71 |
| Min | 51 | 39 |
| Max | 106 | 131 |
| Range | 51-106 | 39-131 |
| n = | 40 | 90 |
| p value | | <0.0001 |

FABP1 levels showed no significant correlation with markers of liver disease, such as AST and γ-GT, in metabolic and healthy donor serum samples as shown in Tables 11 and 12 below. Further to this, there was no significant increase in AST levels in serum between metabolic and control patients. There was, however, a significant increase in γ-GT concentration in serum from metabolic patients compared to the control group (p=0.0056, n=90). This suggests that for metabolic syndrome patients, the determination of an increase in FABP1 ought to be validated with the determination of creatinine, Cystatin C, γ-GT and AST in order to ascertain whether the increase in FABP1 may be due to underlying liver disease, kidney dysfunction or both as co-morbidities.

TABLE 11

| AST (U/L) | | |
|---|---|---|
| | Control | Metabolic |
| Median | 19.5 | 17 |
| Min | 0 | 5 |
| Max | 70 | 91 |
| Range | 0-70 | 5-91 |
| n = | 40 | 90 |
| p value | | 0.22 |

TABLE 12

| gamma-GT (U/L) | | |
|---|---|---|
| | Control | Metabolic |
| Median | 28 | 42 |
| Min | 10 | 11 |
| Max | 187 | 339 |
| Range | 10-187 | 11-339 |
| n = | 40 | 89 |
| p value | | 0.0056 |

Example 7: Determination of FABP1 Thresholds and Classification of CKD Stage Receiver-operator curve (ROC) analysis was employed to determine the specificity and sensitivity for the proposed invention in the first instance to discriminate between control groups and all CKD patients (FIG. 12) and in the second instance to discriminate between Stage 1 (FIG. 13), Stage 2 (FIG. 14) and Stage 3 CKD (FIG. 15). Areas under the curve (AUC) for the ROC for FABP1 being employed to discriminate between control groups and renal disease patients were 0.983 for females (Cut-off>15.65 ng/ml, Sensitivity=0.967, Specificity=1.00) and 0.98 for males (Cut-off>21.6 ng/ml, Sensitivity=0.933, Specificity=1.00). FABP1 showed a respective AUC for females and males of 0.83 (Cut-off>75.8 ng/ml, Sensitivity=0.7, Specificity=0.9) and 0.76 (Cut-off>151.9, Sensitivity=0.5, Specificity=0.9) for discriminating between Stage 2 and Stage 3 CKD. These levels were determined using a cohort of samples collected from a distinct population and therefore normal ranges should be calculated by the end user.

The use of quantitative measurements of FABP1 in conjunction with other potential markers of CKD, such as; cystatin C and creatinine allow discrimination between stage 1 and stage 2 patients. The main clinical differentiation between Stage 1 and Stage 2 is GFR status. Estimated GFR is based on serum levels of either cystatin C or creatinine, with serum concentrations inversely related to GFR. Therefore an elevated FABP1 level (above the lower cut-off value but below the higher cut-off value) combined with elevated cystatin C and/or creatinine compared to the levels suggested in the instructions for use supplied by the manufacturer would classify the patient as Stage 2 CKD, whereas an elevated FABP1 level (above the lower cut-off value but below the higher cut-off value) and a cystatin C and creatinine concentration within the normal range would be classified as Stage 1 CKD. Stage 3 patients are classified based on having a FABP1 concentration above the higher cut-off value and a creatinine and/or cystatin C concentration above the normal range suggested by the assays instructions for use.

Example 8: Algorithm Utilising Serum Levels of FABP1 and Other Analytes to Predict CKD Disease Severity Several methods were employed to identify an optimal panel of multiple biomarkers that would accurately differentiate between CKD and healthy controls and to stratify CKD disease stage. The first was by identifying markers that were individually identified as having a significant predictive value through standard univariant statistics, such as Kruskal-Wallis and Mann-Whitney analysis. This identified FABP1 as being significantly increased in expression in serum in all CKD stages (1, 2 and 3) compared to in serum from healthy volunteers. Furthermore, FABP1 levels are significantly increased in serum from Stage 3 CKD patients compared to Stage 1 and Stage 2 CKD. Both serum creatinine and cystatin C levels were significantly increased in Stage 3 CKD patients compared to healthy volunteers, whilst both AST and γ-GT were unaffected in all disease stages compared to control (despite this it is important to keep these in to rule out liver disease). Cut-off values were determined for FABP1 (as described in example 7) whilst cut-off values for creatinine, cystatin C, AST and γ-GT were defined by the instructions for use of the respective assay by the manufacturer (Randox, UK) and a classification algorithm based on these thresholds was used to predict disease state based on these 5 markers. This resulted in an algorithm which predicted disease severity correctly 71.5% of the time.

Following from this, multinominal logistic regression was employed to investigate if an advanced algorithm could be developed to identify the importance of each marker. A full-factorial model was developed using the concentration of FABP1, creatinine, cystatin C, AST and γ-GT for each disease state and control group, as many of these markers are influenced by gender this was used as a factor in the analysis. This analysis demonstrated that all co-variants and factors (with the exception of cystatin C) had a significant effect on the model. This identified FABP1 and creatinine as the most powerful predictors of disease state. Using the estimated regression coefficients (b), estimated probability ratios could be calculated for each category (Non-CKD [Control], Stage 1, Stage 2 and Stage 3). These ratios could then be used to calculate the estimated probabilities to predict the most probable category a patient may be assigned to, based on the concentrations of FABP1, creatinine, cystatin C, AST and γ-GT. Using this model, disease state could be predicted at a level of 86.2%.

Finally, an artificial neural network was developed using back propagation learning. A smaller randomly assigned set of data was used for training a multilayer perceptron, which was then validated against a hold-out sample of data. Again, the concentration of FABP1 and creatinine were identified as the most important factors for determining disease state. Using a combination of the concentration of all 5 markers, as well as taking into consideration gender, this model could predict disease state with an accuracy of 84%. Although, some markers are not as important as others, it was found that removing these did not improve accuracy.

The results provided in the examples show that the method of the present invention has improved discrimination between the early stages of CKD and controls than prior art methods which suggests that the current invention can be used to aid earlier diagnosis of CKD, thereby providing an advance in clinical diagnosis. The method of the present invention may also be used to stratify patients in groups who are at greater risk of developing CKD as a co-morbidity and provides a means to determine the rate of progression of CKD thereby enabling the clinician to stratify patients who need to be more closely monitored and clinically managed.

An advantage of the methods of the present invention is that serum FABP1 does not require correction for dilution as is the case for urine biomarkers in the prior art. The use of a dilution correction, e.g. creatinine, is fundamentally flawed, given that the correction marker is directly influenced by renal function. Serum FABP1 therefore removes this limitation. 60 serum samples from patients with renal disease were analysed and no such effect was observed. This indicates that serum is a more suitable matrix than urine for the diagnosis and staging of renal disease. Indeed, the results presented in the examples demonstrate that the progressive increase in serum FABP1 associated with disease progression is much more resistant to varying pathological changes within the kidney and, hence, will also be suitable for classification CKD where kidney function is severely impaired.

TABLE 13

| Biomarker | Male | Female | Units | Analyser |
| --- | --- | --- | --- | --- |
| Cystatin C | 0.57-1.05 | 0.57-1.05 | mg/l | RX Daytona, Randox |
| Creatinine | 53-97 | 44-80 | umol/l | RX Daytona, Randox |
| AST | <37 | <31 | U/L | RX Imola, Randox |
| γ-GT | 11.0-50 | 7.0-32 | U/L | RX Imola, Randox |

The invention claimed is:

1. A method of detecting biomarkers of stage 1, 2, 3 or greater of chronic kidney disease (CKD) in a patient suffering from CKD, comprising:
    measuring the level of the biomarkers Fatty Acid-Binding Protein 1 (FABP1), gamma glutamyl transpeptidase (γ-GT), aspartate transaminase (AST), creatinine and cystatin C in a sample obtained from a patient suffering from CKD, and
    determining whether the measured level for each of the biomarkers FABP1, γ-GT, AST, creatinine and cystatin C exceed a lower threshold of a range of control values for each biomarker, wherein at least the measured level for FABP1 exceeds the lower threshold of a range of control values for FABP1 and determining whether the measured levels of γ-GT, AST, creatinine and cystatin C are within the range of control values for each biomarker, or
    wherein the measured levels of γ-GT and AST are within the range of control values for each biomarker, and the measured levels of creatinine and cystatin C exceed the upper threshold of the range of the control for values for these biomarkers, or
    wherein the measured level of FABP1 exceeds the upper threshold of the range of control values of FABP1 and the measured levels of creatinine and cystatin C exceed the upper threshold of the range of the control values for these biomarkers.

2. The method of claim 1, wherein the measured level of the biomarkers are adjusted by the use of a classification algorithm that is derived using logistic regression, decision trees, support vector machines, neural networks, random forest or another machine learning algorithm.

3. The method of claim 1, wherein the sample is a serum sample.

4. The method of claim 1, wherein detecting biomarkers of stage 1 or 2 of CKD, comprises measuring a level of FABP1 from around 15 ng/mL to 75 ng/ml (female) or 21 ng/mL to 151 ng/mL of the biomarkers (male),
    wherein detecting biomarkers of Stage 3 or greater of CKD comprises measuring a level of FABP1 above around 75 ng/mL (female) or 151 ng/mL (male) of the biomarkers.

5. The method of claim 1, wherein the patient has co-morbidity for a renal disease or injury selected from the group consisting of, but not limited to, chronic kidney disease (CKD), acute kidney injury (AKI), diabetic nephropathy, glomerulonephritis, focal glomerulosclerosis, immune complex nephropathy, lupus nephritis, drug-induced renal injury, or is characterized as nephrotic syndrome or renal insufficiency or is caused by kidney graft rejection.

6. The method of claim 1, wherein the patient has metabolic syndrome.

7. The method of claim 1, wherein the level of the biomarkers is measured comprising using a solid state device comprising a substrate having an activated surface on to which is immobilized an antibody to FABP1 in discreet areas of the activated surface.

8. The method of claim 7, wherein the antibody to FABP1 is a monoclonal antibody.

9. The method of claim 7, wherein the substrate has an activated surface on to which is immobilized an antibody to γ-GT or AST.

10. The method of claim 9, wherein the antibody to γ-GT or AST is a monoclonal antibody.

11. The method of claim 7, wherein the substrate has an activated surface on to which is immobilized an antibody to cystatin C or creatinine.

12. The method of claim 11, wherein the antibody to cystatin C or creatinine is a monoclonal antibody.

13. The method of claim 9, wherein the substrate has an activated surface on to which is immobilized an antibody to cystatin C or creatinine.

14. The method of claim 13, wherein the antibody to cystatin C or creatinine is a monoclonal antibody.

15. The method of claim 7, further comprising: indicating that the patient suffers from stage 1, 2, 3 or above of CKD based upon the measured level of the biomarkers.

16. A method of detecting biomarkers of stage 1, 2, 3 or greater of chronic kidney disease (CKD) in a patient suffering from CKD, comprising:
   measuring the level of the biomarkers Fatty Acid-Binding Protein 1 (FABP1), gamma glutamyl transpeptidase (γ-GT), aspartate transaminase (AST), creatinine and cystatin C in a sample obtained from a patient suffering from CKD, and
   determining whether the measured level for each of the biomarkers FABP1, γ-GT, AST, creatinine and cystatin C exceed a lower threshold of a range of control values for each biomarker, wherein at least the measured level for FABP1 exceeds the lower threshold of a range of control values for FABP1, and
   wherein detecting biomarkers of stage 1 or 2 of CKD, further comprises measuring a level of FABP1 from around 15 ng/mL to 75 ng/ml (female) or 21 ng/mL to 151 ng/mL of the biomarkers (male), and
   wherein detecting biomarkers of Stage 3 or greater of CKD comprises measuring a level of FABP1 above around 75 ng/mL (female) or 151 ng/mL (male) of the biomarkers.

17. A method of detecting biomarkers of stage 1, 2, 3 or greater of chronic kidney disease (CKD) in a patient suffering from CKD, comprising:
   measuring the level of the biomarkers Fatty Acid-Binding Protein 1 (FABP1), gamma glutamyl transpeptidase (γ-GT), aspartate transaminase (AST), creatinine and cystatin C in a sample obtained from a patient suffering from CKD, and
   determining whether the measured level for each of the biomarkers FABP1, γ-GT, AST, creatinine and cystatin C exceed a lower threshold of a range of control values for each biomarker, wherein at least the measured level for FABP1 exceeds the lower threshold of a range of control values for FABP1, and
   indicating that the patient suffers from stage 1, 2, 3 or above of CKD based upon the measured level of the biomarkers,
   wherein the level of the biomarkers is measured comprising using a solid-state device comprising a substrate having an activated surface on to which is immobilized an antibody to FABP1 in discreet areas of the activated surface.

\* \* \* \* \*